United States Patent [19]

Vera-Castaneda et al.

[11] Patent Number: 4,740,272
[45] Date of Patent: Apr. 26, 1988

[54] SEPARATION OF MONOALKYL MALEATE FROM DIALKYL MALEATE

[75] Inventors: Ernesto Vera-Castaneda, Webster, Tex.; Diane A. Montevideo, Given; David J. Miller, Charleston, both of W. Va.; John E. Logsdon, Houston, Tex.; David R. Bryant, South Charleston, W. Va.

[73] Assignee: Davy McKee (London) Limited, London, England

[21] Appl. No.: 32,259

[22] Filed: Mar. 31, 1987

[51] Int. Cl.[4] .......................... B01D 3/14; C07C 67/54
[52] U.S. Cl. ......................................... 203/74; 203/77; 203/81; 203/89; 203/DIG. 19; 549/326; 560/190; 560/191; 560/204; 568/864
[58] Field of Search ............. 203/74, 77, 81, DIG. 19, 203/99, 89, 19; 560/191, 190, 204; 568/864; 549/326

[56] References Cited

U.S. PATENT DOCUMENTS

| | | | |
|---|---|---|---|
| 2,333,666 | 11/1943 | Moore et al. | 560/190 |
| 2,938,837 | 5/1960 | Meyer et al. | 203/77 |
| 3,681,204 | 8/1972 | Mercier | 203/77 |
| 3,979,443 | 9/1976 | Schwartz et al. | 560/204 |
| 4,032,458 | 6/1977 | Cooley et al. | 560/190 |
| 4,584,419 | 4/1986 | Sharif et al. | 568/864 |

FOREIGN PATENT DOCUMENTS

| | | | |
|---|---|---|---|
| 24818 | 2/1979 | Japan | 560/190 |
| 1245568 | 7/1986 | U.S.S.R. | 560/190 |

OTHER PUBLICATIONS

Chemical Abstracts, vol. 67, No. 25, Dec. 18, 1967, p. 10964 Abst. No. 116, 520 g, Gordinskii, B. Y. et al., "Preparation and Separation of Pure Monoalkyl Maleates".

Primary Examiner—Wilbur Bascomb
Attorney, Agent, or Firm—Bernard, Rothwell & Brown

[57] ABSTRACT

A method of producing substantially pure dialkyl maleate by separating monoalkyl maleate from dialkyl maleate in a short residence time distillation zone while minimizing reversion of the monoalkyl maleate to alkanol and maleic anhydride and without having to neutralize the monoalkyl maleate.

49 Claims, 3 Drawing Sheets

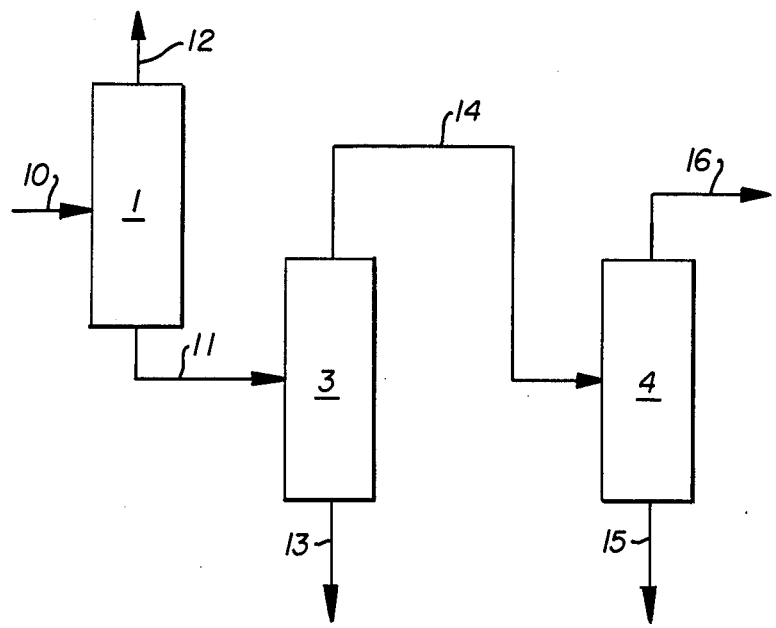
F I G. 1
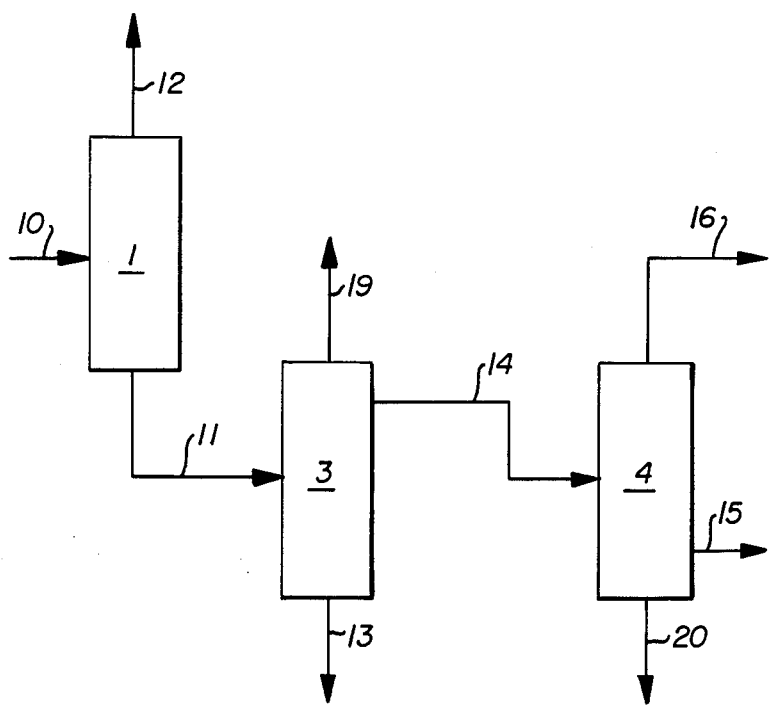
F I G. 2

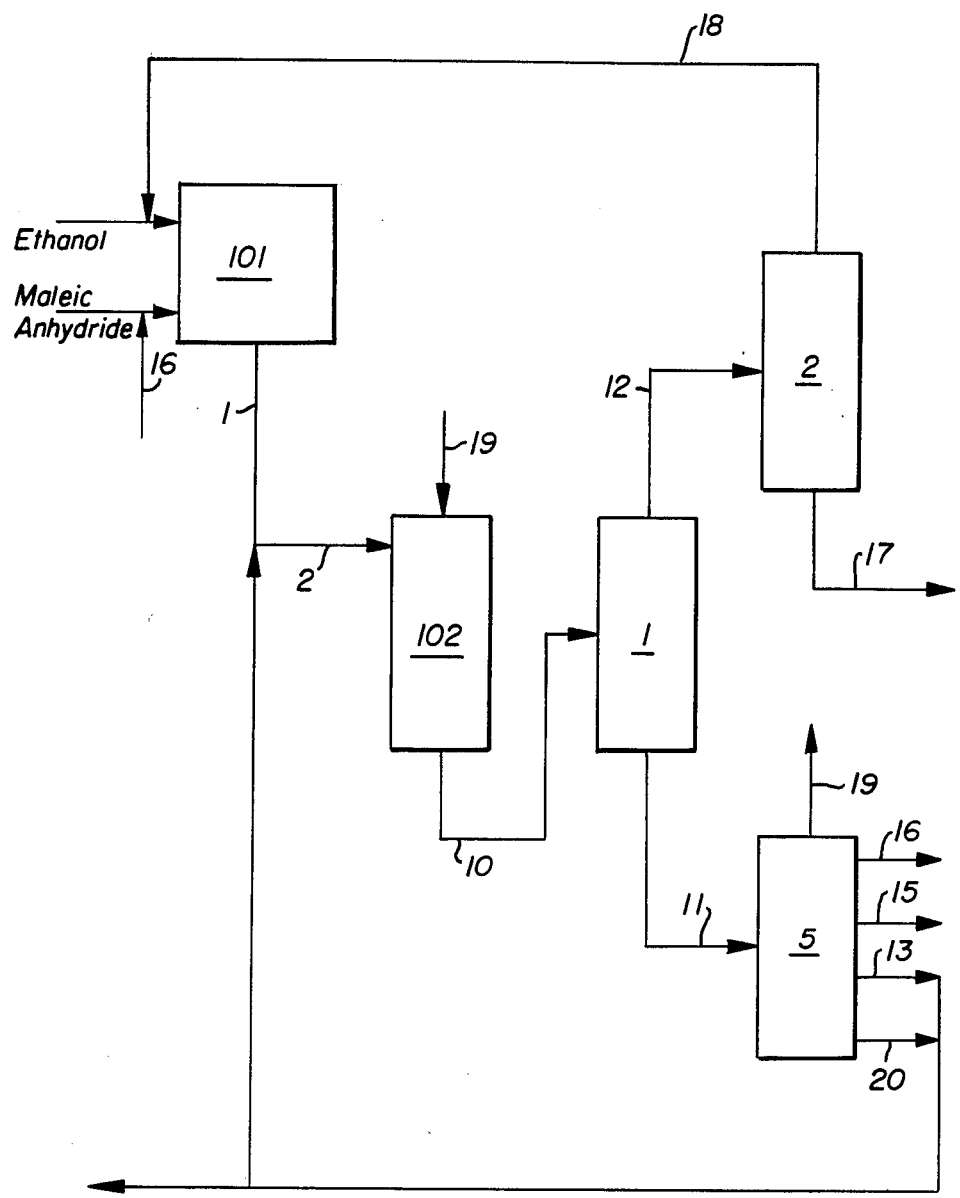

4,740,272

SEPARATION OF MONOALKYL MALEATE FROM DIALKYL MALEATE

BACKGROUND OF THE INVENTION

1. Field of the Invention

The subject invention relates to a method of separating dialkyl maleate from monoalkyl maleate to produce essentially pure dialkyl maleate while minimizing reversion of monoalkyl maleate to maleic anhydride and alkanol. The invention also relates to a method of producing substantially pure dialkyl maleate free of maleic anhydride, monoalkyl maleate, and alkanol from maleic anhydride by advantageously utilizing this separation method.

2. Description of the Related Art

Production of 1,4-butanediol, gamma-butyrolactone, and tetrahydrofuran from maleic anhydride is typically carried out in stages. According to a known procedure, maleic anhydride first is esterified with ethanol to produce monoethyl maleate. This reaction proceeds rapidly without catalyst. The monoethyl maleate then is esterified with ethanol to produce diethyl maleate. The second esterification can be catalyzed if desired. Water is a by-product. The desired 1,4-butanediol, gamma-butyrolactone, and tetrahydrofuran products are obtained from diethyl maleate by hydrogenolysis, using, for example, a catalyst such as that disclosed in Sharif, U.S. Pat. No. 4,584,419.

To maximize the life of the hydrogenation catalyst, it is desirable that the dialkyl maleate be essentially free of monoalkyl maleate. One technique of obtaining dialkyl maleate free of monoalkyl maleate is to obtain essentially complete conversion in the esterification stages of the process.

The monoethyl maleate to diethyl maleate reaction is typically catalyzed in a first reactor, such as a stirred tank or plug flow reactor, until the conversion level is about 70 percent. Because the reaction is an equilibrium reaction, the water present precludes obtaining higher conversion levels in a single reactor. Instead, to obtain complete conversion of monoethyl maleate to diethyl maleate, a water/ethanol mixture is removed and dry ethanol is fed to additional reactors. The equilibrium nature of the reaction requires that an essentially dry reaction system be maintained in the reactor in which complete conversion is obtained.

The requirement that water be removed from the reaction system to shift the equilibrium and allow the reaction to go to completion imposes a substantial burden on such an operation. For example, removal of water from the mixture also entails the removal of substantial quantities of ethanol, because these components form an azeotrope. To obtain dry ethanol for the process, the water must be separated in an energy-intensive and costly separation.

The alternative to completion of the reaction, neutralizing the mono-esterified component of the incompletely-esterified stream with base, is also unsatisfactory. Not only is reactant wasted, but additional costs are incurred in producing a diethyl maleate stream free of monoethyl maleate. A costly waste-treatment facility will be required. The monoethyl maleate which is neutralized is lost, e.g. by delivery to a waste treatment facility unless the base stream is acidified and the monoethyl maleate extracted, adding yet additional cost to the system. Also, the consumption of base imposes an additional cost on the process.

High purity diester product is necessary because the diethyl maleate is utilized, inter alia, as a reactant in the production of 1,4-butanediol by catalytic hydrogenolysis, and the catalyst commonly used for this reaction typically is deactivated by carboxylic acids such as monoethyl maleate.

In a process requiring complete conversion of monoethyl maleate to the diester, the expense associated with completely dehydrating ethanol and of maintaining a dry reaction system is significant. The alternative approach, wherein monoethyl maleate is neutralized, is technically and commercially feasible only when monoethyl maleate is present at low concentrations. Therefore, a method of physically separating monoethyl maleate from diethyl maleate would be desirable. However, such a method heretofore has been unavailable.

Attempts to separate monoethyl maleate from diethyl maleate by distillation have been unsuccessful because monoethyl maleate reverts to maleic anhydride and ethanol at conditions typically required to effect the separation, i.e., when using conventional residence time, high temperature distillations. Monoethyl maleate exposed to these conditions reverts to ethanol and maleic anhydride at the bottom of the distillation tower. At the top of the tower, ethanol and maleic anhydride recombine to yield monoethyl maleate. Therefore, a substantial internal flow develops within the distillation column, causing severe operational difficulty. Further, monoethyl maleate is removed from the tower in the tails, which contain primarily diethyl maleate, thus defeating the purpose of the separation, viz, to produce pure diethyl maleate free of monoethyl maleate. Thus, production of pure diethyl maleate is impossible if this technique alone is used.

It is an object of this invention to substantially completely separate dialkyl maleate from monoalkyl maleate, such as diethyl maleate from monoethyl maleate, by distillation while minimizing reversion of the monoalkyl maleate to maleic anhydride and alkanol (ethanol), and without having to neutralize the monoalkyl maleate.

It is a further object of this invention to produce substantially pure diethyl maleate without having to use anhydrous ethanol to convert monoethyl maleate to diethyl maleate.

SUMMARY OF THE INVENTION

In accordance with these and other objects, this invention relates to a method of separating dialkyl maleate from a mixture containing monoalkyl maleate and dialkyl maleate which minimizes reversion of monoalkyl maleate to maleic anhydride and the corresponding alkanol comprising: introducing said mixture into a first distillation zone wherein the residence time is less than about 30 minutes and distilling said mixture in the first distillation zone into a monoalkyl maleate-rich bottoms fraction and a dialkyl maleate-rich overhead fraction. Further, this invention also relates to the separation method wherein said dialkyl maleate-rich overhead fraction is further distilled in a second distillation zone.

This invention also relates to a method of producing substantially pure dialkyl maleate by reacting an alkanol with maleic anhydride to produce monoalkyl maleate and then reacting said monoalkyl maleate with said alkanol to produce a mixture containing dialkyl maleate, monoalkyl maleate, alkanol, and by-product water, the improvement comprising: separating any unreacted alkanol and by-product water from said mixture to produce a monoalkyl maleate- and dialkyl maleate-containing stream; introducing said stream into a first distillation zone wherein the residence time is less than about 30 minutes; and fractionating said stream in the first distillation zone into a monoalkyl maleate-rich bottoms fraction and a dialkyl maleate-rich overhead fraction. If desired, said dialkyl maleate-rich overhead fraction is further distilled in a second distillation zone.

BRIEF DESCRIPTION OF THE DRAWINGS

FIG. 1 is a schematic diagram of an embodiment of the method of this invention.

FIG. 2 is a schematic flow diagram of a preferred embodiment of the method of this invention.

FIG. 3 is a schematic flow diagram of the advantageous use of the invention in the preparation of substantially pure dialkyl maleate.

On the drawings, like numbers are utilized to identify like parts.

DETAILED DESCRIPTION OF THE INVENTION

As those skilled in the art recognize, minor amounts of fumaric acid or its esters may be present with the maleic acid or the maleic esters. For example, fumaric acid will exist with maleic acid; dialkyl maleate may have a minor fraction of diethyl fumarate, and so on. For the purpose of this invention, such minor amounts of fumaric acid or esters can be treated as the corresponding maleic form unless otherwise noted. Therefore, in this specification and in the claims, the definition of a maleic component also includes the fumaric components.

The present invention is based on the discovery that substantially pure dialkyl maleate can be produced using maleic anhydride and an alkanol by separating dialkyl maleate from a mixture containing dialkyl maleate and monoalkyl maleate using fractional distillation while minimizing reversion of monoalkyl maleate to said alkanol and maleic anhydride and without having to neutralize monoalkyl maleate. This method is advantageously used to produce substantially pure dialkyl maleate.

The alkanols which have 2 to 4 carbon atoms are suitable for use within the broad scope of this invention. Examples of such alkanols include ethanol, n-propanol, i-propanol, n-butanol, 1-methyl propanol, 2-methyl propanol, and t-butyl alcohol. Alkanols having either 2 or 3 carbon atoms are preferred, while ethanol is more preferred. For the sake of convenience, the invention will be described with reference to ethyl alcohol (ethanol) as the alkanol. The scope of the invention is, however, to be limited only by the appended claims.

Those skilled in the art will appreciate that diethyl maleate can be converted to 1,4-butanediol, gamma-butyrolactone, and tetrahydrofuran by catalytic hydrogenolysis. Catalysts presently known for this hydrogenolysis, such as reduced copper chromite, are deactivated by acids and acid anhydrides, e.g., monoethyl maleate, maleic acid, maleic anhydride, and the like. Therefore, diethyl maleate utilized in this catalytic process must be substantially free of acids. The method of this invention produces such a diethyl maleate stream.

For a related reason, water also should be removed from the diethyl maleate-containing stream to avoid producing maleic acid by a reversion reaction with monoethyl maleate or diethyl maleate. As noted above, maleic acid would deactivate certain hydrogenolysis catalysts. Similarly, fumarates present will produce, in the presence of water, a minor amount of fumaric acid. Fumaric acid poses yet an additional problem as it sublimes at the conditions maintained in the distillation zones and deposits as a solid in the overhead piping after the overhead stream is cooled in a condenser. Removal of water in the initial stages of the process reduces the likelihood that such acids will be formed.

Ethanol also should be removed from the product stream, because it reacts with maleic anhydride in the distillation zones to produce monoethyl maleate, which may later revert to ethanol and maleic anhydride elsewhere in the zone. This process causes a substantial internal reflux within the zone. Therefore, it is preferred to remove the ethanol early in the process.

The method taught by this invention enables production of pure diethyl maleate, free of significant amounts of monoethyl maleate, maleic acid, and maleic anhydride from a mixture containing some or all of these components. At conditions typically considered necessary for purification of diethyl maleate by distillation, monoethyl maleate would revert to form maleic anhydride and ethanol at the bottom of the tower, while conditions at the top of the tower would allow the ethanol and maleic anhydride to recombine and form monoethyl maleate. Thus, in a traditional distillation, a large internal reflux would be established within the tower, and, more importantly, monoethyl maleate would be removed in the tails, i.e., with the diethyl maleate product, thereby defeating the object of the separation. These difficulties are avoided by the method of this invention.

Referring to FIG. 1, stream 10 may be the product of a catalytic esterification of monoethyl maleate with ethanol to produce diethyl maleate and by-product water. The exact composition of the stream is not critical to the practice of the method of this invention. A typical range of compositions which could be utilized in the method of this invention is given in Table 1.

TABLE 1

| Range of Typical Compositions of Product Stream 10 from Conversion of Monoethyl Maleate to Diethyl Maleate | |
|---|---|
| Component | Typical Range, wt. percent |
| Diethyl maleate | 20–80 |
| Monoethyl maleate | 0.5–40 |
| Water | 5–40 |
| Ethanol | 10–60 |
| Maleic Anhydride | 0.0–1.0 |

As noted in Table 1, stream 10 generally contains water and ethanol. Preferably, these constituents are removed preliminarily, if present. Typically, this separation is advantageously done in distillation zone 1, as shown on FIG. 1, although other means of removing ethanol and water from the other components are known to those skilled in the art.

Distillation zone 1 is operated as required to yield bottoms product 11 containing between about 50 and about 98 weight percent diethyl maleate and between about 2 and about 50 weight percent monoethyl maleate, and having a water concentration less than about 5 weight percent, preferably less than about 0.5 weight percent, and more preferably less than about 0.3 weight percent; an ethanol concentration less than about 10 weight percent, preferably less than about 1 weight percent, and more preferably less than about 0.5 weight percent; a maleic acid concentration less than about 2 weight percent, preferably less than about 0.3 weight percent, and more preferably less than about 0.2 weight percent; and a maleic anhydride concentration of less than about 5 weight percent, preferably less than about 1 weight percent, and more preferably less than about 0.5 weight percent.

Distillation zone 1 preferably is a distillation tower. The design details and mode of operation are a matter of choice. The selection of, for example, the cooling fluid in the condenser would depend inter alia on the composition of stream 10. The composition of overhead 12 from distillation zone 1 is dependent upon the composition of streams 10 and 11.

Various combinations of pressure and temperature can be maintained in distillation zone 1 to achieve a bottoms product composition within the ranges described above. As recognized by those skilled in the art, the temperatures required at the top and bottom of the tower to achieve the preferred composition ranges for stream 11 are related to the pressure maintained in the tower. In the practice of this invention, the average pressure in distillation zone 1 is within the range of about 0.1 to 30 psia. Temperature ranges which correspond to this preferred pressure range are between about $-10°$ to $100°$ C. at the top and between about $70°$ to $280°$ C. at the bottom of the tower.

At the more preferred pressure range of about 2 to 15 psia, the temperature range for the overhead is about $30°$ to $80°$ C. while the corresponding range for the bottoms is about $140°$ to $260°$ C. When the most preferred pressure range of about 2–10 psia is utilized, the temperature of the overhead will be between about $30°$ and $70°$ C. while the temperature at the bottom will be between about $140°$ and $220°$ C.

The present invention is based on the discovery that monoethyl maleate in the bottoms product 11 from distillation zone 1 can be separated from diethyl maleate while minimizing reversion of monoethyl maleate to maleic anhydride and ethanol and without having to neutralize monoethyl maleate by effecting the separation within a distillation zone 3 designed to have a short residence time and operated at relatively low temperatures. Stream 11 is separated in distillation zone 3 into a diethyl maleate-rich overhead fraction in line 14 and a monoethyl maleate-rich bottom fraction in line 13.

Distillation zone 3 may be provided with a reboiler and a condenser (not shown) needed to generate the reflux liquid and vapor for fractionating the feed. Equipment can be selected by those skilled in the art, and will depend inter alia upon the actual composition of stream 11 to be treated, the purity desired in overhead product stream 14, and the operating conditions and equipment selected. For example, although film evaporators may not be provided with a reboiler, some vapor-generation source should be provided. A variety of operating conditions exist for distillation zone 3 which yield the desired substantially pure diethyl maleate stream.

The preferred average pressure in distillation zone 3 is between about 0.1 to 30 psia. More preferably, the pressure is between about 2 to 15 psia, and most preferably is between 2 to 10 psia. This pressure level is determined commercially by the temperature of the fluid utilized to cool the overhead stream. For example, an overhead temperature of about $30°$ C. might be selected, because cooling water is typically available at an appropriate temperature. At this temperature, a pressure of about 3 psia would be preferred.

The ranges of temperatures corresponding to the useful pressure ranges are about $7°-280°$ C. in the reboiler and about $-10°$ to $100°$ C. at the overhead condenser of distillation zone 3 (pressure range of 0.1–30 psia); preferably about $140°-260°$ C. at the bottom and about $30°-80°$ C. at the overhead (preferred pressure range of 2–15 psia); and most preferably, about $140°-220°$ C. at the bottom and about $30°-70°$ C. at the overhead.

The temperature of feed stream 11 and the location of the introduction of feed into distillation zone 3 are both based on the composition of the stream and the operating pressure and temperature for the separation. Preferably, the feed temperature will be between about $25°$ and $260°$ C., more preferably between about $25°$ and $210°$ C. Those skilled in the art will be able to determine where to locate the feed introduction point. Typically, between about 50 to 75 theoretical stages are required in distillation zone 3.

Distillation zone 3 need not be and preferably is not a trayed distillation tower. The separation can be achieved in short residence time distillation zones such as packed columns, wiped film evaporators, and falling film evaporators, referred to herein as film evaporators. Examples of such evaporators can be found in *Perry's Chemical Engineers' Handbook*, pages 11-24 through 11-49 (4th Ed. 1969). In fact, any distillation-type purification apparatus which can be operated at the desired residence time of less than about 30 minutes can be used. Residence time is defined as ratio of zone hold-up volume to volumetric feed rate. The residence time in the method of the invention does not exceed about 30 minutes, is preferably less than about 10 minutes, and most preferably is less than about 5 minutes. A film evaporator preferably would be provided with a rectification section for vapor leaving the evaporator. This rectification section could be a few short residence time distillation trays, a packed column, or the like. This section provides additional rectification for the overhead and a convenient location for a side stream draw. The number of actual stages depends upon not only the degree of separation required, but also the feed composition. Film evaporators can provide very short residence times, typically less than about 3 minutes. Packed columns will provide longer residence times, at least about 10 minutes. The packing can be Berl saddles, perforated semi-cylinders, or any commercial packing providing adequate vapor/liquid contact. As described above, the maximum residence time is about 30 minutes.

Although sieve trays could also be utilized in distillation zone 3, it may be difficult to obtain the short residence times required. Those skilled in the art are able to establish reflux and boil-up ratios consistent with minimizing residence time. For example, those skilled in the art appreciate that as boil-up ratio increases, residence time increases. Therefore, the boil-up ratio preferably is less than about 50, more preferably is less than about 30.

Although residence times of less than about 30 minutes can be achieved in a trayed distillation zone, those skilled in the art recognize that such an operation would not be very efficient. Further, the residence times obtainable in thin film evaporators are considerably shorter, e.g., from a few seconds to five minutes. Because falling film and wiped film evaporators have a much shorter residence time than do packed or trayed columns, evaporators are preferred.

Packed columns also are preferred over trayed columns for distillation zone 3 because packed columns have less hold-up volume, and therefore yield shorter residence times. Dumped packing or ordered packing is acceptable. However, ordered packing is preferred because it affords better performance. Because ordered packing has very low pressure drop, lower temperatures and pressures can be used in the separation process.

Examples of dumped packing include Raschig rings, Lessing rings, partition rings, Berl saddles, Intalox saddles, Tellerette, and Pall rings. Examples of ordered packing are sold by under the trade names Goodloe, Hyperfil, Neo-Kloss, Koch-Sulzer, and Laval film trays.

As illustrated in the embodiment shown in FIG. 1, stream 14 is taken overhead as product from distillation zone 3. Although the composition of this stream will vary, it is preferably at least about 60 weight percent diethyl maleate, less than 1.0 weight percent monoethyl maleate, less than about 40 weight percent maleic anhydride, less than about 20 weight percent ethanol, and possibly a trace (less than about 0.5 weight percent) of maleic acid. More preferably, the diethyl maleate concentration is at least about 75 weight percent, the monoethyl maleate concentration is less than or equal to 1.0 weight percent, the ethanol concentration is less than about 5 weight percent, and the maleic anhydride concentration is less than about 10 weight percent; they may be a trace of maleic acid. Bottoms stream 13 contains monoethyl maleate and other heavy components.

The extremely short residence times required by the present invention and best achieved in film evaporators substantially reduce the amount of monoethyl maleate which reverts to maleic anhydride and ethanol. Thus, where feed 11 is essentially ethanol- and maleic anhydride-free and the amount of reversion is minimal, overhead stream 14 may have a diethyl maleate concentration exceeding 98 weight percent, the remainder being essentially monoethyl maleate; essentially no maleic anhydride will be present. The virtual absence of maleic anhydride and low acid concentration eliminate the need to further distill the diethyl maleate-rich stream in distillation zone 4 is stream 14 has the desired composition. However, if further purification of the diethyl maleate is desired or necessary, diethyl maleate-rich overhead stream 14 is separated in distillation zone 4 to yield separate streams, one substantially pure diethyl maleate stream 15, the other an ethanol- and maleic anhydride-containing stream 16 (originating in part from reversion of the monoethyl maleate).

Although the pressure ranges in distillation zone 3 are also suitable for distillation zone 4, higher pressures and thus higher temperatures can be used in distillation zone 4 because there is less opportunity for adverse reactions, such as the reversion of monoethyl maleate to maleic anhydride and ethanol, to occur. Thus, stream 14 can be heated and pumped by means not shown to a higher temperature an pressure before being fractionated in distillation zone 4. Stream 14 may be at a pressure of between about 0.02-100 psia. Stream 14 generally will be fed into distillation zone 4 at a temperature between about 25° to 300° C., preferably between about 25°-210° C.

Distillation zone 4 is maintained at a pressure of between about 0.02-100 psia, preferably between about 0.1-30 psia, more preferably about 2-15 psia, and most preferably between about 2-10 psia. At pressures within these ranges, bottoms temperatures typically are between about 70°-300° C., preferably between about 80°-280° C., more preferably between about 100°-270° C., and most preferably between about 100°-250° C. Corresponding overhead temperatures typically are between about 30° to 270° C., preferably between about 50° to 260° C., more preferably between about 70° to 250° C., and most preferably between about 70° to 225° C. Distillation zone 4 should be operated so that its condenser is maintained at a temperature above the solidification point of maleic anhydride to prevent deposition of maleic anhydride in the overhead equipment.

Distillation zone 4 can be any of the types of equipment described for distillation zone 3. However, in distillation zone 4, sieve trays can be utilized throughout, as the residence time in distillation zone 4 is less critical than the residence time in distillation zone 3.

The inventors prefer to recover in stream 15 at least about 50 percent, preferably at least about 70 percent, more preferably at least about 90 percent, and most preferably at least about 95 percent, of the diethyl maleate in stream 11. Further, because acids are known to deactivate many hydrogenolysis catalysts, it is preferred to achieve an acid concentration in the diethyl maleate of less than about 1 percent, preferably less than 0.5 percent, and most preferably less than about 0.1 percent.

Product stream 15 is preferably maintained at a diethyl maleate concentration greater than about 99 weight percent with maleic anhydride and monoethyl maleate less than 1 weight percent. More preferably, the diethyl maleate concentration of this stream is 99.5 percent, and most preferably the concentration is 99.9 percent, with the other component concentrations reduced proportionately. These preferred product qualities are obtained by processing stream 11 in the distillation zones 3 and 4. Use of two distillation zones allows optimization of the operating conditions in each zone.

Overhead product stream 16 from distillation zone 4 can be returned to the esterification reactor, if desired, to supply maleic anhydride for the reactor.

FIG. 2 illustrates a schematic flow diagram of a preferred embodiment of this invention wherein a stream containing maleic anhydride and diethyl maleate is withdrawn from distillation zone 3 as a side stream 14. In the process, overhead stream 19 contains primarily ethanol and lighter components, while monoethyl maleate and heavier components are taken off as bottoms 13. Removal of the ethanol helps prevent formation of monoethyl maleate in maleic anhydride/diethyl maleate-containing side stream 14. Overhead 19 and bottoms 13 can be returned to various steps within the reaction process, if desired. The preferred ranges of operating conditions (pressure, flow rate, residence time, and the like) are the same as those preferred in the embodiments illustrated in FIG. 1.

In accordance with the embodiment illustrated in FIG. 2, distillation zone 3 is operated to achieve at least about 50 weight percent recovery of diethyl maleate. Preferably, diethyl maleate recovery is at least about 70 weight percent, more preferably is at least about 90 weight percent, and most preferably is at least about 95 weight percent.

When the composition of feed stream 11 is within the limits described above and the targeted diethyl maleate recoveries are achieved, overhead stream 19 contains at least about 50, preferably at least about 70, more preferably at least about 90, and most preferably at least about 98 weight percent ethanol; less than 50 weight percent, preferably less than about 30 weight percent, more preferably less than about 10, and most preferably less than about 2 weight percent maleic anhydride; and less than about 20 weight percent, preferably less than about 10 weight percent, more preferably less than about 5 weight percent, and most preferably less than about 1 weight percent diethyl maleate.

Under these conditions, bottoms stream 13 contains preferably less than about 70 weight percent, more preferably less than about 50 weight percent, and most preferably less than about 5 weight percent diethyl maleate; preferably at least about 30 weight percent, more preferably at least about 50 weight percent, and most preferably at least about 95 weight percent monoethyl maleate; and preferably less than about 0.5 weight percent, more preferably less than about 0.1 weight percent, and most preferably less than about 0.05 weight percent maleic anhydride.

Maleic anhydride/diethyl maleate-containing stream 14 is subsequently separated in distillation zone 4. If distillation zone 3 is operated in the preferred manner, stream 14 contains at least about 60 weight percent, preferably at least about 75 weight precent, and more preferably at least about 98 weight percent diethyl maleate; less than about 50 weight percent, generally less than about 40 weight precent, and more typically less than about 35 weight percent maleic anhydride; less than about 40 weight percent, generally less than about 10 weight percent, and more typically less than about 1 weight percent monoethyl maleate; less than about 1 weight percent, preferably less than about 0.5 weight percent, and more preferably less than about 0.01 weight percent maleic acid; and less than about 1 weight percent, preferably less than about 0.01 weight percent water.

As shown in FIG. 2, any remaining monoethyl maleate and heavy components are removed as bottoms 20. Maleic anhydride is recovered as overhead stream 16 and diethyl maleate product is recovered as side stream 15. If desired, overhead 16, overhead 19, and bottoms 20 can be recycled to the esterification reaction process.

Every effort is made to prevent reversion of monoethyl maleate to maleic anhydride and ethanol. However, these reactive constituents will unavoidably be present because esterification is an equilibrium reaction. Therefore, the embodiment illustrated in FIG. 2, which takes advantage of the concentration profiles within distillation zones 3 and 4, is preferred.

Those skilled in the art will recognize that concentration profiles will be established in the distillation zone 3. At the top of the zone 3, the maleic anhydride and ethanol concentrations will be at their highest while the monoethyl maleate concentration will be at its lowest. At the bottom of the zone, the opposite is true. Therefore, referring to FIG. 2, because the ethanol will be removed from the zone in overhead stream 19, taking stream 14 as a side stream allows one to draw a diethyl maleate-rich stream having a lower ethanol concentration than would typically be produced in stream 14 of the FIG. 1 embodiment. However, the monoethyl maleate concentration may be higher. As noted above, both monoethyl maleate and maleic anhydride are undesirable as constituents in the diethyl maleate stream because they both deactivate the hydrogenolysis catalyst.

The location of side stream 14 in the preferred embodiment illustrated in FIG. 2 is affected by presence of water in stream 11. If water is present, the location of the side draw will be lower than when water is not present, so that little, if any, water is carried into side stream 14. This increase in the distance from the tops helps ensure that the water is kept out of distillation zone 4, where it might react with maleic anhydride to produce deleterious maleic acid. Maleic acid (and the fumaric acid associated with the maleic acid) would be more likely to be deposited as a solid within the equipment. Water thus should be taken overhead with any remaining ethanol as stream 19, which can be recycled to the monoethyl maleate-to-diethyl maleate esterification reactor. Bottoms stream 13 contains the monoethyl maleate and other heavy components.

In a similar fashion, the side draw of diethyl maleate stream 15 from distillation zone 4 has the advantage over bottoms draw 15 of FIG. 1 of providing a purer diethyl maleate product, because any deleterious material and trace components such as salts, residual monoethyl maleate and heavy polymeric substances are removed in bottoms 20. No such opportunity exists in the embodiment disclosed in FIG. 1. Side draw 15 preferably is maintained with a diethyl maleate concentration greater than about 99 percent, preferably greater than about 99.8 weight percent, with maleic anhydride and monoethyl maleate less than 1 percent, preferably less than about 0.1 weight percent each.

In the embodiment exemplified in FIG. 2, bottoms 20 of distillation zone 4 preferably has a composition of less than about 0.5 weight percent maleic anhydride, at least about 30 weight percent monoethyl maleate, and less than about 70 weight percent diethyl maleate. More preferably, the composition of bottoms 20 is less than about 0.1 weight percent maleic anhydride, at least about 50 weight percent monoethyl maleate, and less than about 50 weight percent diethyl maleate. Most preferably, bottoms 20 contains less than 0.05 weight percent maleic anhydride, at least about 95 weight percent monoethyl maleate and less than about 5 weight percent diethyl maleate. Overhead stream 16 contains 60-100 weight percent, preferably at least about 80 weight percent maleic anhydride and less than about 40 weight percent, preferably less than about 20 weight percent diethyl maleate.

Typically, distillation zone 4 is operated at a pressure between about 0.02 to 100 psia, preferably between about 0.1-30 psia, more preferably between about 2-15 psia, and most preferably between about 2-10 psia. Feed stream 14 is typically supplied at a temperature between about 25° to 300° C., preferably between about 25° to 210° C. Therefore, the desired separations can be achieved if the temperature at the bottom of the zone is maintained between about 70° to 300° C., preferably between about 80°-280° C., more preferably between about 100° to 270° C., and most preferably between about 100°-250° C., while the temperature at the top of zone typically is maintained between about 30° to 270° C., preferably between about 50°-260° C., more preferably between about 70° to 250° C., and most preferably between about 70° to 225° C.

FIG. 3 illustrates a preferred embodiment for the manufacture of diethyl maleate from maleic anhydride. This method uses the advantages resulting from the discovery of the present method of separating monoethyl maleate from diethyl maleate. The operation is greatly simplified, and anhydrous ethanol is not required.

As schematically illustrated in FIG. 3, product stream 10 from the catalytic esterification of monoethyl maleate to diethyl maleate in reactor 102 is fractionated in accordance with this invention. Ethanol and water are separated in distillation zone 1 as overhead in stream 12 from the remainder of the constituents in stream 11. Stream 11 is further fractionated in distillation zone or zones 5 to yield a monoethyl maleate-containing stream 13, desired diethyl maleate product 15, and a maleic anhydride stream 16. Further, an ethanol and water stream 19 and a monoethyl maleate- and heavies-containing stream 20 may be produced.

Each of these streams can advantageously be utilized in the monoethyl maleate to diethyl maleate reaction scheme. Ethanol and water stream 12 is subsequently partially dehydrated in distillation zone 2. Those skilled in the art recognize that ethanol and water form an azeotrope. The water concentration of this azeotrope is sufficiently low for use of the azeotropic composition as an ethanol source for the initial maleic anhydride esterification reaction when recycled as stream 18 to reactor 101, as shown in FIG. 3. Alternatively, the ethanol concentration of this stream may be increased by partially dehydrating the stream or by admixing the stream with another ethanol stream having a lower water concentration. Maleic anhydride stream 16 may form a part of the maleic adhydride feed to reactor 101. The uncatalyzed esterification of maleic anhydride to monoethyl maleate occurs in reactor 101.

These two recycle streams, plus fresh maleic anhydride and ethanol, are fed to reactor 101. The fresh ethanol need not be bonedry for this stage of esterification. Therefore, a substantial saving can be realized in the manufacture of diethyl maleate by following the method of this invention.

An excess of ethanol is fed to reactor 101 so that product stream 1 from reactor 101 contains monoethyl maleate, unreacted ethanol, water, and small quantities of other constituents. Monoethyl maleate and heavy component stream 13 can be recycled in whole or in part and combined with reactor 101 product stream 1 to form feed 2 to reactor 102. In this reactor, monoethyl maleate is catalytically esterified to diethyl maleate.

In reactor 102, typically 70 percent of the monoethyl maleate is converted to diethyl maleate. The product in stream 10 from reactor 102 contains, inter alia, diethyl maleate, by-product water, and unreacted monoethyl maleate and ethanol.

The following examples are intended to illustrate further the invention, not to limit its scope. The scope of the invention is limited only by the claims.

EXAMPLE 1

This example reports the results of a computer simulation of a 50 theoretical stage continuous multi-stage distillation of stream 11, containing 3.2 weight percent ethanol, 0.2 weight percent maleic acid, 7.3 weight percent maleic anhydride, 81.0 weight percent diethyl maleate, and 8.3 weight percent monoethyl maleate. The simulation of distillation zone 3 was in accordance with the preferred embodiment illustrated in FIG. 2. The ethanol and maleic anhydride concentrations were established assuming that 50 weight percent of the monoethyl maleate had reverted to ethanol and maleic anhydride. Therefore, the concentrations of ethanol and maleic anhydride in actual operations would typically be lower. However, the purpose of the simulation was to ensure that the separation in distillation zone 3 could be achieved even with this assumed high reversion level.

Distillation zone 3 was operated at a pressure of 4 psia, a reflux ratio of 65, and a boil-up ratio of 50. The feed was introduced at the 40th theoretical tray (numbered from the top) at a temperature of 130° C. The overhead condenser was operated at 48° C., so that ambient cooling water could be used. The reboiler was operated at 196° C., utilizing 70 psig steam. The residence time was about 25 minutes.

Under these conditions, an overhead stream 19 comprising 100 weight percent ethanol, and a sidestream 14 containing 0.07 weight percent ethanol, 0.23 weight percent maleic acid, 8.27 weight percent maleic anhydride, 91.43 weight percent diethyl maleate, and a trace of monoethyl maleate were produced. The sidestream was withdrawn from the eighth theoretical tray from the top. Bottoms stream 13 contained 97.21 1 weight percent monoethyl maleate and 2.79 weight percent diethyl maleate. The overhead flow rate was 3.1 percent, the sidestream was 88.3 percent, and the bottoms flow rate was 8.5 percent of the feed mass flow rate.

This example illustrates the low ethanol and monoethyl maleate concentrations in sidestream 14 in the preferred embodiment, even at an unrealistically high monoethyl maleate reversion rate.

EXAMPLE 2

This example presents the results of a computer simulation of a 20 theoretical stage continuous multi-stage distillation separation of stream 14, containing 0.3 weight percent maleic acid, 8.0 weight percent maleic anhydride, and 91.7 weight percent diethyl maleate. The feed was fed to the 15th theoretical stage of distillation zone 4, in accordance with FIG. 1. The distillation zone was operated at an average pressure of 4 psia, with a reflux ratio of 25. The overhead temperature was 150° C., allowing use of cooling water, and the reboiler temperature was 177° C., utilizing 200 psig steam.

Overhead stream 16, which had a mass flow rate of 10.2 weight percent of the feed mass flow rate, contained 2.95 weight percent maleic acid, 78.44 weight percent maleic anhydride, and 13.61 weight percent diethyl maleate. Bottoms stream 15, which had a mass flow rate of 89.8 weight percent of the feed mass flow rate, contained 0.02 weight percent maleic anhydride and 99.98 weight percent diethyl maleate.

This example illustrates that a diethyl maleate stream essentially free of maleic anhydride and maleic acid can be produced.

EXAMPLE 3

Stream 11, as defined in Example 1, was fractionated in a computer simulation of distillation zone 3, as described in Example 1, in accordance with an embodiment of FIG. 2. The distillation zone was operated at a pressure of 4 psia, utilizing 70 theoretical trays, a reflux ratio of 65, and a boil-up ratio of 50. The feed was introduced at the 55th theoretical tray (numbered from the top) at a temperature of 130° C. The overhead condenser was operated at 48° C. using ambient cooling water. Steam at 70 psig was used to raise the bottoms temperature to 196° C. The residence time was about 30 minutes.

Under these conditions, overhead stream 19 was 100 percent ethanol and has a mass flow rate of 3.1 percent of the feed mass flow rate. A first side stream (not shown) was withdrawn at the 15th theoretical stage.

This stream had a mass flow rate of 9.4 percent of the feed mass flow rate and contained 0.74 weight percent ethanol, 2.07 weight percent maleic acid, 71.79 weight percent maleic anhydride, and 25.40 weight percent diethyl maleate.

A second sidestream (Stream 14) was withdrawn at the 35th theoretical stage at a mass flow rate of 78.9 percent of the feed mass flow rate. This stream contained traces of ethanol and maleic acid, 0.66 weight percent maleic anhydride, 99.29 weight percent diethyl maleate, and 0.04 weight percent monoethyl maleate. Bottoms stream 13 contained 96.28 weight percaent monoethyl maleate and 3.72 weight percent diethyl maleate. The mass flow rate was 8.6 percent of the feed mass flow rate.

This example illustrates that excellent separations can be made using a method of this invention to produce relatively pure ethanol, diethyl maleate, and monoethyl maleate product streams. The diethyl maleate stream has very low concentrations of ethanol and monoethyl maleate, and the monoethyl maleate is relatively pure.

EXAMPLE 4

Computerized multi-stage separation techniques were utilized to simulate separation of an 82.1 weight percent diethyl maleate/17.9 weight percent monoethyl maleate stream in distillation zone 3, modeled as a wiped film evaporator over which three trays had been placed for additional rectification of the vapors. The residence time was 30 seconds. The evaporator pressure was 0.5 psi and the overhead temperature was 129° C.

Two simulations were made. In the first, 90 percent of the diethyl maleate in the feed was recovered in the overhead. The bottoms temperature required was 147° C. In the second, 95 percent of the diethyl maleate was recovered; a bottoms temperature of 156° C. was required.

When 90 percent of the diethyl maleate was recovered, the overhead composition was 98.9 weight percent diethyl maleate and 1.1 weight percent monoethyl maleate, while the bottoms contained 32.5 weight percent diethyl maleate and 67.5 weight percent monoethyl maleate.

When 95 percent of the diethyl maleate was recovered, the overhead composition remained unchanged, although the bottoms contained only 19.5 weight percent diethyl maleate and 80.5 weight percent monoethyl maleate.

These examples illustrate that, when no monoethyl maleate reverts to maleic anhydride and ethanol, only one distillation zone is required to obtain a diethyl maleate stream which can be hydrogenated without additional treatment.

Although preferred embodiments of this invention have been disclosed herein, those skilled in the art will appreciate that changes and modifications may be made without departing from the spirit of this invention, as defined in and limited only by the scope of the appended claims. For example, a plurality of distillation zones can be used to effect the separation of monoethyl maleate from diethyl maleate within the preferred residence time.

We claim:

1. A method for separating dialkyl maleate from a mixture containing monoalkyl maleate and dialkyl maleate, each having the same alkyl group of between 2 and 4 carbon atoms, which minimizes reversion of monoalkyl maleate to maleic anhydride and the corresponding alkanol, said method comprising:
   (a) introducing said mixture into a first distillation zone wherein the residence time of said mixture is less than about 30 minutes;
   (b) distilling said mixture in the first distillation zone at a pressure between about 0.1 to 30 psia into a monoalkyl maleate-rich bottoms fraction and a dialkyl maleate-rich overhead fraction; and
   (c) further distilling the dialkyl maleate-rich overhead fraction in a second distillation zone, at a pressure between about 0.02–100 psia, to produce a high purity dialkyl maleate product.

2. The method of claim 1 wherein the alkyl group has 2 or 3 carbon atoms.

3. The method of claim 2 wherein the pressure in said first distillation zone is between about 2 to 15 psia.

4. The method of claim 3 wherein the pressure in said first distillation zone is between about 2 to 10 psia.

5. The method of claim 2 wherein the pressure in said second distillation zone is between about 0.1 to 30 psia.

6. The method of claim 5 wherein the pressure in said second distillation zone is between about 2 to 15 psia.

7. The method of claim 6 wherein the pressure in said second distillation zone is between about 2 to 10 psia.

8. The method of claim 2 wherein the residence time is less than about 10 minutes.

9. The method of claim 8 wherein the residence time is less than about 5 minutes.

10. The method of claim 2 wherein the purity of said dialkyl maleate product is at least about 99 weight percent.

11. The method of claim 10 wherein the purity of said dialkyl maleate product is at least about 99.5 weight percent.

12. The method of claim 2 wherein the alkyl group has 2 carbon atoms.

13. The method of claim 12 wherein the pressure in said first distillation zone is between about 2 to 15 psia.

14. The method of claim 13 wherein the pressure in said first distillation zone is between about 2 to 10 psia.

15. The method of claim 12 wherein the pressure in said second distillation zone is between about 0.1 to 30 psia.

16. The method of claim 15 wherein the pressure in said second distillation zone is between about 2 to 15 psia.

17. The method of claim 16 wherein the pressure in said second distillation zone is between about 2 to 10 psia.

18. The method of claim 12 wherein the residence time is less than about 10 minutes.

19. The method of claim 18 wherein the residence time is less than about 5 minutes.

20. The method of claim 12 wherein the purity of said dialkyl maleate product is at least about 99 weight percent.

21. The method of claim 20 wherein the purity of said dialkyl maleate product is at least about 99.5 weight percent.

22. A method for separating dialkyl maleate from a mixture containing monoalkyl maleate and dialkyl maleate, each having the same alkyl group of between about 2 and 4 carbon atoms, which minimizes reversion of monoalkyl maleate to maleic anhydride and the corresponding alkanol, said method comprising:

(a) introducing said mixture into a first distillation zone wherein the residence time of said mixture is less than about 30 minutes;
(b) distilling said mixture in the first distillation zone at a pressure between about 2 to 10 psia into a monoalkyl maleate-rich bottoms fraction and a dialkyl maleate-rich overhead fraction; and
(c) further distilling the dialkyl maleate-rich overhead fraction in a second distillation zone wherein the pressure is between about 2 to 10 psia to produce a dialkyl maleate product having a purity of at least about 99 weight percent.

23. The method of claim 22 wherein the alkyl group has 2 or 3 carbon atoms.

24. The method of claim 23 wherein the residence time is less than about 10 minutes.

25. The method of claim 24 wherein the residence time is less than about 5 minutes.

26. The method of claim 23 wherein the alkyl group has 2 carbon atoms.

27. The method of claim 26 wherein the residence time is less than about 10 minutes.

28. The method of claim 27 wherein the residence time is less than about 5 minutes.

29. In a method of producing dialkyl maleate by reacting an alkanol having 2 to 4 carbon atoms with maleic anhydride to produce monoalkyl maleate and then reacting said monoalkyl maleate with the alkanol to produce a stream containing dialkyl maleate, by-product water, and unreacted monoalkyl maleate, the improvement comprising:
(a) separating any unreacted alkanol and by-product water from said stream to produce a mixture containing monoalkyl maleate and dialkyl maleate;
(b) introducing said mixture into a first distillation zone wherein the residence time is less than about 30 minutes;
(c) distilling said mixture in said first distillation zone at a pressure between about 0.1 to 30 psia into a monoalkyl maleate-rich bottoms fraction and a dialkyl maleate-rich overhead fraction; and
(d) further distilling said diethyl maleate-rich overhead fraction at a pressure between about 0.02–100 psia in a second distillation zone to produce a high purity dialkyl maleate product.

30. The method of claim 20 wherein the alkanol has 2 or 3 carbon atoms.

31. The method of claim 30 wherein the pressure in said first distillation zone is between about 2 to 15 psia.

32. The method of claim 31 wherein the pressure in said distillation zone is between about 2 to 10 psia.

33. The method of claim 30 wherein the pressure in said second distillation zone is between about 0.1 to 30 psia.

34. The method of claim 33 wherein the pressure in said second distillation zone is between about 2 to 15 psia.

35. The method of claim 34 wherein the pressure in said second distillation zone is between about 2 to 10 psia.

36. The method of claim 30 wherein the purity of said diethyl maleate product is at least about 99 weight percent.

37. The method of claim 36 wherein the purity of said diethyl maleate product is at least about 99.5 weight percent.

38. The method of claim 30 wherein the residence time is less than about 10 minutes.

39. The method of claim 38 wherein the residence time is less than about 5 minutes.

40. The method of claim 29 wherein the alkanol is ethanol.

41. The method of claim 40 wherein the pressure in said first distillation zone is between about 2 to 15 psia.

42. The method of claim 41 wherein the pressure in said distillation zone is between about 2 to 10 psia.

43. The method of claim 40 wherein the pressure in said second distillation zone is between about 0.1 to 30 psia.

44. The method of claim 43 wherein the pressure in said second distillation zone is between about 2 to 15 psia.

45. The method of claim 44 wherein the pressure in said second distillation zone is between about 2 to 10 psia.

46. The method of claim 40 wherein the purity of said diethyl maleate product is at least about 99 weight percent.

47. The method of claim 46 wherein the purity of said diethyl maleate product is at least about 99.5 weight percent.

48. The method of claim 40 wherein the residence time is less than about 10 minutes.

49. The method of claim 48 wherein the residence time is less than about 5 minutes.

* * * * *